(12) United States Patent
Sirota

(10) Patent No.: US 9,289,196 B2
(45) Date of Patent: Mar. 22, 2016

(54) HEMOSTATIC SUBSTANCE WITH A COATING

(75) Inventor: Daniel J. Sirota, Bloomington, IN (US)

(73) Assignee: COOK MEDICAL TECHNOLOGIES LLC, Bloomington, IN (US)

(*) Notice: Subject to any disclaimer, the term of this patent is extended or adjusted under 35 U.S.C. 154(b) by 1186 days.

(21) Appl. No.: 11/954,352

(22) Filed: Dec. 12, 2007

(65) Prior Publication Data

US 2008/0160051 A1 Jul. 3, 2008

Related U.S. Application Data

(60) Provisional application No. 61/874,393, filed on Dec. 12, 2006.

(51) Int. Cl.
| | | |
|---|---|---|
| *A61K 9/00* | (2006.01) | |
| *A61K 38/39* | (2006.01) | |
| *A61K 38/43* | (2006.01) | |
| *A61B 17/00* | (2006.01) | |
| *C08L 1/00* | (2006.01) | |
| *A61K 38/48* | (2006.01) | |
| *A61L 27/20* | (2006.01) | |
| *A61L 27/54* | (2006.01) | |
| *A61K 38/36* | (2006.01) | |

(52) U.S. Cl.
CPC ......... *A61B 17/0057* (2013.01); *A61K 38/4833* (2013.01); *A61L 27/20* (2013.01); *A61L 27/54* (2013.01); *C08L 1/00* (2013.01); *A61B 2017/00004* (2013.01); *A61B 2017/00654* (2013.01); *A61B 2017/00884* (2013.01); *A61B 2017/00893* (2013.01); *A61K 38/363* (2013.01); *A61K 38/39* (2013.01); *A61L 2300/418* (2013.01); *A61L 2300/45* (2013.01); *A61L 2300/606* (2013.01); *A61L 2400/04* (2013.01)

(58) Field of Classification Search
None
See application file for complete search history.

(56) References Cited

U.S. PATENT DOCUMENTS

| | | | |
|---|---|---|---|
| 4,329,332 A | 5/1982 | Couvreur et al. | |
| 4,597,960 A * | 7/1986 | Cohen | 424/435 |
| 4,954,298 A | 9/1990 | Yamamoto et al. | |
| 5,061,492 A | 10/1991 | Okada et al. | |
| 5,100,669 A | 3/1992 | Hyon et al. | |
| 5,330,767 A | 7/1994 | Yamamoto et al. | |
| 5,595,735 A * | 1/1997 | Saferstein et al. | 424/94.64 |
| 5,651,990 A | 7/1997 | Takada et al. | |
| 6,056,970 A * | 5/2000 | Greenawalt et al. | 424/426 |
| 6,264,988 B1 | 7/2001 | Yen | |
| 6,391,343 B1 | 5/2002 | Yen | |
| 6,534,091 B1 * | 3/2003 | Garces Garces et al. | 424/489 |
| 6,568,398 B2 * | 5/2003 | Cohen | 128/898 |
| 2004/0091543 A1 * | 5/2004 | Bell et al. | 424/489 |
| 2006/0229670 A1 * | 10/2006 | Bates | 606/213 |

* cited by examiner

*Primary Examiner* — Bethany Barham
*Assistant Examiner* — Dominic Lazaro
(74) *Attorney, Agent, or Firm* — Brinks Gilson & Lione

(57) ABSTRACT

A hemostatic device includes a dissolvable coating and a hemostatic substance enclosed within the coating. The device can have, for example, a generally spherical shape. The hemostatic substance can be particles that take any shape, such as spherical, flat sheets, cubes, or other regular or irregular shapes of any size or volume that can be used on or within a body.

11 Claims, 1 Drawing Sheet

HEMOSTATIC SUBSTANCE WITH A COATING

CROSS-REFERENCE TO RELATED APPLICATIONS

This application claims the benefit of U.S. Provisional Application Ser. No. 60/874,393, filed on Dec. 12, 2006, entitled "HEMOSTATIC SUBSTANCE WITH A COATING," the entire contents of which are incorporated herein by reference.

BACKGROUND

This invention relates to a substance coated with a dissolvable coating or covering.

A hemorrhage of a blood vessel, body tissue, organ or bone can result in blood loss leading to shock and death. Many of these fatalities can be prevented if blood loss at the particular site is minimized. For example, fibrin has been employed as a coagulating substance to stop bleeding and to seal wounds. These "fibrin glues" are typically based on a two component system of fibrinogen and thrombin which when mixed form a fibrin coagulum. These components, however, have a water-like fluidity that makes them difficult to handle and administer.

As an alternative to fibrin glue, a biodegradable collagen patch in the form of a collagen carrier such as a foam, web or film that is coated with a mixture of blood-clotting components including fibrinogen and thrombin has been employed. However, optimum timing of the fixing procedure of the active components onto the collagen carrier is difficult to obtain. Furthermore, the active components are not able to penetrate beyond the surface of the collagen carrier, which limits the concentration of blood-clotting components available to the surface of the patch.

Accordingly, there is a need for hemostatic devices that are less complicated to use than those described above.

SUMMARY

A hemostatic device includes a dissolvable coating and a hemostatic substance enclosed within the coating. The device can have, for example, a generally spherical shape. The hemostatic substance can be particles that take any shape, such as spherical, flat sheets, cubes, or other regular or irregular shapes of any size or volume that can be used on or within a body. The hemostatic substance may take various forms, such as hemostatic lipid, that is, Hemos, a hemostatic collagen, or a hemostatic that is a synthetic. The hemostatic substance generally begins the process of hemostasis upon contact with blood or blood components.

Further objects, features, and advantages of the present invention will become apparent from consideration of the following description and the appended claims when taken in connection with the accompanying drawings.

DETAILED DESCRIPTION

Figure 1:
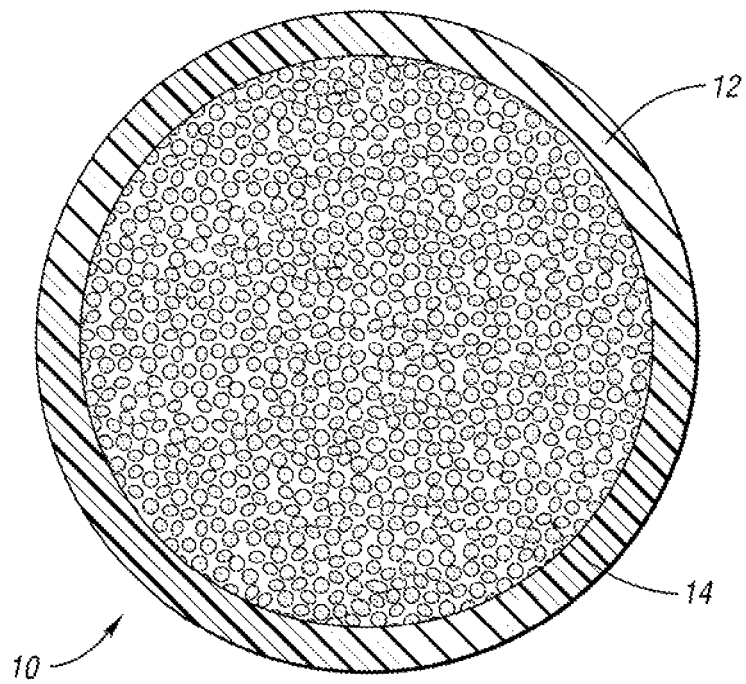
FIG. 1 is a cross-sectional view of a spherical hemostatic device in accordance with an embodiment of the invention.
Figure 2:
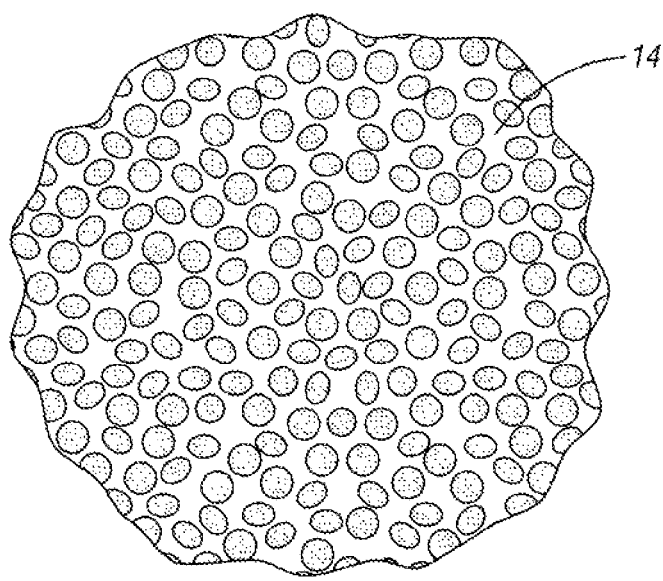
FIG. 2 is a close-up view of hemostatic particles associated with the hemostatic device of FIG. 1.

Referring now to FIG. 1, a hemostatic device embodying the principles of the present invention is illustrated therein and designated at 10. As its primary components, the hemostatic device includes a dissolvable or bioabsorpable coating 12 and a hemostatic substance 14 enclosed within the coating 12. The coating 12 dissolves after delivery to a location of interest allowing hemostasis to begin, thus providing time for the hemostatic substance 14 to reach a particular destination on or within the body. The coating 12 may dissolve instantaneously or over a longer period of time, for example, within about one to several seconds. A hemostatic substance, as used herein, is a substance that, upon application to a wound reduces or stops blood loss by promoting blood clot formation.

In a particular implementation, the hemostatic substance is made of hemostatic particles. The particles may take any regular or irregular shape of any size or volume that can be used on or within a patient's body. For example, the particle may be spherical, as shown, or they may be flat sheets or cubes.

The hemostatic substance 14 may be a hemostatic liquid, that is, HEMOS, or a hemostatic collagen. The substance 14 may be a synthetic. In a particular implementation, the hemostatic substance is thrombin that may contain a calcium salt, such as calcium chloride. In certain implementations, the substance 14 includes fibrinogen.

Hemostatic materials that may be used include, but are not limited to, HEMOS, Fibrin Adhesive Material (Tissucol®), Epsilon-Aminocaproic Acid (EACA), Chitosan, poly-N-acetylglucosamine (p-GlcNAc), Microporous Polysaccharide Hemosphere (MPH), QR powder, hemostatic lipids, and other suitable hemostatic materials, or mixtures thereof. Another hemostatic material, namely platelet aggregating material from equine arterial tissue, has been previously described in U.S. Pat. No. 4,374,830, the entire contents of which are incorporated herein by reference.

Other suitable hemostatic materials known to those skilled in the art may also be used in accordance with this invention.

A hemostatic material may include, for example, HEMOS, the chemical structure of which is shown in Formula 1 below.

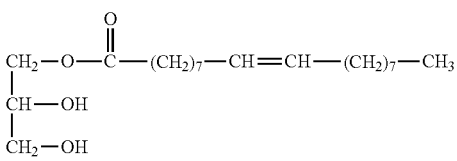

Formula 1

HEMOS is a monoglyceride that is obtained by esterifying glycerol with oleic acid from olive oil. HEMOS is widely used in the food industry as emulsifier and in pharmaceuticals as a drug carrier. HEMOS is characterized in that it is able to stop bleeding when applied to a hemorrhaging surface. HEMOS, when formulated with about 5% water content and epinephrine, exists as a liquid that can be poured, pumped, sprayed, mixed or otherwise applied to wound sites. Upon contacting blood, HEMOS absorbs fluid to form a wax-like structured "cubic" phase. The oil-like consistency of HEMOS allows for mixing of this hemotactic material with an ECM material. Preferably, HEMOS is mixed with ECM material in a fluidized or gel-like form, prepared as described above. The ECM material provides the necessary structural component of this composition, while HEMOS allows to control bleeding and to restore hemostasis.

Manufacturing of HEMOS may involve two simple steps, as follows:

1. HEMOS, which is a white waxy solid in the pure state, may be prepared as a liquid by adding water for a final content of about 5%. Vasoactive, antimicrobial, and other small compounds may be added with the water. Mixtures may be sterilized by elevating the temperature.

2. The liquid HEMOS may be packaged as a liquid or composed with sponges, matrix, etc. as required, for example with the ECM material as described herein. A terminal sterilization with heat may be performed.

HEMOS may be composed with an ECM material to form a composition comprising the ECM material and HEMOS. Such composition is prepared for delivery to seal a puncture site in a wall of a blood vessel, as part of the closure system.

The thrombin and the fibrinogen can be of animal or human origin. The thrombin and the fibrinogen may include natural thrombin and fibrinogen molecules, respectively, derived from animal or human plasma, and synthetic forms such as those produced by recombinant DNA technology including functionally active analogs that effectively maintain clotting activity in an animal or human. The concentration of calcium chloride used in various implementations allows for activation of the thrombin. The fibrinogen can be highly purified, can contain small amounts of clotting factor XIII, or can be enriched with clotting factor XIII.

Additional blood-clotting constituents and fibrinolysis inhibitors can also be included in the hemostatic substance 14. Examples include, but are not limited to, Factor XIII, fibronectin, plasminogen, aprotinin, alpha-2-antiplasmin, alpha-2 macroglobulin, alpha-1-antitrypsin, epsilon-aminocaproic acid or tranexamic acid, or a plasmin activator inhibitor, e.g., PAI-1 or PAI-2.

In a further embodiment, the hemostatic substance can also contain an amount of the agent protamine sulfate effective to neutralize heparin present in the local environment of the area of application. Protamine sulfate neutralizes heparin or vitamin K antagonists that are present in the blood of certain patients.

The hemostatic substance 14 may have within it medications which can be released at the time the coating 12 dissolves. In addition to the hemostatic agents, the substance 14 can further contain components which promote wound healing and prevent infection such as, but not limited to polypeptide growth factors, non-steroidal anti-inflammatory agents, antibiotics, and cytostatics. The concentrations of the additional components vary depending on the desired objective. The amount of each component can be readily determined by empirically testing various concentrations and selecting that which is effective for the intended purpose and the site of interest.

The coating 12 is generally a bioabsorbable material. For example, the coating 12 can be bioabsorbable polymers, such as polyanionic polysaccharides, alginic acid, chitin, chitosan, fibrin, polyglycolide, polylactide, polycaprolactone, dextran and copolymers thereof.

In a particular implementation, the bioabsorbable polymer is a polyanionic polysaccharide. For example, the polyanionic polysaccharide may be HA, CMC or CMA which is in the form of a water-insoluble derivative. In yet other implementations, the polyanionic polysaccharide is combined with one or more hydrophobic bioabsorbable polymers or copolymers.

The hemostatic device 10 can be employed for topical treatment to inhibit or stop bleeding of wounds due to trauma or surgery. Or the hemostatic device 10 may be employed to inhibit or stop bleeding of an organ, such as the liver, kidney, spleen, pancreas, or lungs. Alternatively, the device 10 may be employed to stop bleeding or fluid loss during surgery including, but not limited to, abdominal, vascular, urological, gynecological, thyroidal, neurosurgery, tissue transplant, and dental surgery.

The hemostatic substance 14 can also be provided for use to fuse ends of a blood vessel or other body lumen that has been severed, for example, during surgery. For instance, the hemostatic device 10 can be provided in a form that easily fits to the ends of a vascular prosthesis. In cases where the vascular prosthesis is synthetic, such as a Dacron graft, the hemostatic device 10 can be provided in a form (for example, cylindrical) sized to easily fit over the ends of the graft.

The hemostatic device 10 can be provided in a variety of shapes which are useful for packing into body cavities, including, but not limited to, spherical, conical, cuboidal or cylindrical shapes. Moreover, embodiments of the present invention may be used in stopping blood flow within a vessel, vein or artery for treatment of chronic or traumatic injury or physical abnormalities such as pulmonary arteriovenous malformation (PAVM).

The hemostatic device 10 mentioned above may be used for other various treatments. For example, the device 10 may be used to treat a tumor in a patient. That is, the device 10 may be used to prevent blood supply to a tumor in a patient. In this example, the device 10 may be used as an embolic occlusion apparatus to stop blood flow to a benign or malignant tumor, e.g., a fibroid in the uterus or gastrointestinal track of a patient.

While the present invention has been described in terms of preferred embodiments, it will be understood, of course, that the invention is not limited thereto since modifications may be made to those skilled in the art, particularly in light of the foregoing teachings.

What is claimed is:

1. A hemostatic device comprising:
an outer coating that dissolves over a period of time, the outer coating surrounding an interior volume, the interior volume being free of material of the coating; and
a plurality of hemostatic particles disposed inside the interior volume of the outer coating, hemostasis occurring when the hemostatic particles contact blood or blood components after being released by the outer coating upon a sufficient dissolution of the outer coating;
the outer coating being dimensioned to free the entire plurality of hemostatic particles simultaneously at a predetermined time for being released and sized to fit one of a blood vessel, a body cavity, and a vascular prosthesis.

2. The device of claim 1 wherein the device is generally spherical.

3. The device of claim 1 wherein the particles are generally spherical.

4. The device of claim 1 wherein the hemostatic particles include a hemostatic lipid.

5. The device of claim 1 wherein the hemostatic particles include a synthetic.

6. The device of claim 1 wherein the hemostatic particles further include a calcium salt.

7. The device of claim 1 wherein the hemostatic particles include one or more drugs that are released when the coating dissolves.

8. The device of claim 1 wherein the coating is bioabsorbable.

9. The device of claim 8 wherein the coating is a bioabsorbable polymer.

10. The device of claim 1 wherein the hemostatic particles include thrombin.

11. The device of claim 1 wherein the period of time is predetermined to allow time for the hemostatic particles to reach a particular destination within the body before the coating releases the plurality of particles.

* * * * *